United States Patent [19]

Au

[11] 4,266,054
[45] May 5, 1981

[54] N-SUBSTITUTED PERHYDRO-S-TRIAZINES

[75] Inventor: Andrew T. Au, Needham, Mass.

[73] Assignee: The Dow Chemical Company, Midland, Mich.

[21] Appl. No.: 148,302

[22] Filed: May 9, 1980

Related U.S. Application Data

[63] Continuation-in-part of Ser. No. 32,600, Apr. 23, 1979, abandoned.

[51] Int. Cl.$^3$ ............................................. C07D 251/04
[52] U.S. Cl. ..................................................... 544/215
[58] Field of Search .......................................... 544/215

[56] References Cited

U.S. PATENT DOCUMENTS

| | | | |
|---|---|---|---|
| 2,809,942 | 10/1957 | Cooke | 544/215 |
| 3,462,381 | 8/1969 | Eaton et al. | 544/215 |
| 3,840,661 | 10/1974 | Waldstein | 544/215 |
| 3,915,970 | 10/1975 | Limaye et al. | 544/215 |
| 3,937,716 | 2/1976 | Lewis et al. | 544/215 |

*Primary Examiner*—John M. Ford
*Attorney, Agent, or Firm*—David H. Fifield; Douglas N. Deline

[57] ABSTRACT

N-substituted perhydro-s-triazine compounds can be used to increase the solubility of alkali or alkaline earth metal salts in an organic medium. Increasing the solubility of such salts catalyzes the reaction between the salts and other components of the organic medium. For example, 5 percent of a tris(n-octylpolyoxyethylene)-N,N',N"-perhydro-3-triazine compound catalyzes the reaction between sodium iodide and n-octyl bromide at 80° C. for 1 hour to form 100 percent yield of n-octyl iodide.

5 Claims, No Drawings

N-SUBSTITUTED PERHYDRO-S-TRIAZINES

CROSS-REFERENCE TO RELATED APPLICATION

This is a continuation-in-part of parent application Ser. No. 32,600, filed Apr. 23, 1979, now abandoned.

BACKGROUND OF THE INVENTION

This invention pertains to polyoxyalkylene-N-substituted perhydro-s-triazine compounds and their use in solubilizing alkali or alkaline earth metal salts in an organic medium.

Glycol ethers are known to complex alkali and alkaline earth metal ions. For example, in U.S. Pat. No. 2,435,524, ethylene glycol dialkyl ethers participate in complex formation with KOH.

The concept of octopus molecules is proposed by Vögtle and Weber in "Octopus Molecules", *Angew. Chem. Internat., Edit.* 13, 814 (1974). Octopus molecules are multi-armed polyether, complex-forming ligands that contain donor atoms. Polyether-substituted benzene and pyridine compounds are studied where the polyether "arms" are joined to the ring substrate by sulfide linkages.

Fornasier and Montanari discuss the phase-transfer capacities of "polypode" ligands in "Polypode Ligands as Phase-Transfer Catalysts", *Tetrahedron Letters*, 17, 1381 (1976). Many of the compounds are carbon-substituted derivatives of triazines.

A. M. Paquin in *Berichte*, 82, 316 (1949) describes a process for forming tris(hydroxyalkyl)-N,N',N"-substituted perhydro-s-triazines from ethanolamine and formaldehyde. This compound does not exhibit significant phase-transfer properties.

SUMMARY OF THE INVENTION

This invention comprises a compound of the formula

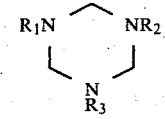

wherein $R_1$, $R_2$, and $R_3$ are each independently $(-A-)_n R_4$, where $-A-$ is independently, each occurrence $-CHRCHR'O-$ wherein R and R' are hydrogen or methyl, provided that at most only one of R or R' is methyl, $R_4$ is independently, each occurrence, H or a $C_{1-40}$ alkyl radical, and n is independently, each occurrence, a number from 2 to about 40, and the use of said compound for solubilizing alkali or alkaline earth metal salts in an organic medium.

DETAILED DESCRIPTION OF THE INVENTION

The compounds of this invention, N-substituted perhydro-s-triazine polyethers represented by Formula I

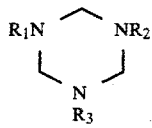

wherein $R_1$, $R_2$, and $R_3$ are as previously defined (hereafter compounds of Formula I are referred to as PTP's) are prepared from inexpensive materials.

A. M. Paquin in *Berichte*, 82, 316, 320 (1949) discusses the procedure for making a precursor (Z) to PTP's. Ethanolamine is reacted with formaldehyde to produce a compound represented by

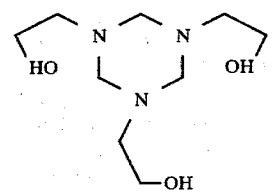

Precursor Z

This Precursor Z is condensed with a 1,2-alkylene oxide in the presence of a basic catalyst, such as sodium, sodium hydroxide or potassium hydroxide, to form alkyleneoxy adducts of Z, which are hydroxy-terminated. The reaction is suitably run at a temperature from about 105° C. to about 110° C. for about 2–3 hours. Ambient pressure is used for convenience, but at a higher pressure the reaction will proceed more rapidly. The amount of 1,2-alkylene oxide needed is 3n equivalents with n corresponding to the number of alkyleneoxy units desired. A mixture of 1,2-alkylene oxides may be employed to produce heteric adducts or different 1,2-alkylene oxides may be reacted sequentially to produce "blocked" adducts.

The hydroxy-terminated adducts can be capped with an alkyl moiety, $R_4$. Capping the adduct with a terminal alkyl by reaction with a suitable hydrocarbon improves the ability of the PTP to dissolve alkali and alkaline earth metal salts. Any alkyl group can be utilized to form the termination group, including straight, branched and cyclic alkyl moieties, and aryl-substituted alkyl moieties, e.g., tolyl. The hydrocarbon must be capable of undergoing a Williamson condensation reaction with the terminal hydroxyl of the above-described adducts of Z. Suitable reactants are, for example, $R_4Cl$ and $R_4Br$. Preferably $R_4$ is $C_{1-15}$ alkyl. The capping reaction is suitably carried out at a temperature from about 25° C. to about 60° C. If complete capping is desired, excess $R_4Cl$ or $B_4Br$ should be used, i.e., at least 3 equivalents for every equivalent of the hydroxy-terminated adduct. Capping may be carried out in any non-polar solvent. Inexpensive, common solvents are preferred.

The alkyleneoxy units in the PTP's are preferably ethyleneoxy or propyleneoxy groups. Examples of suitable PTP's include compounds of Formula I where A is ethyleneoxy, n is 40, and $R_4$ is H; A is ethyleneoxy and propyleneoxy in random formation, n is 15, and $R_4$ is $C_4H_9$; A is alternately ethyleneoxy and propyleneoxy forming a "blocked" adduct, n is 5.5, and $R_4$ is tolyl; A is propyleneoxy, n is 4, and $R_4$ is $C_8H_{17}$; A is ethyleneoxy, n is 5.5, and $R_4$ is $C_8H_{17}$; and the like. It should be understood that the number n is an average value, being one-third of the total moles of 1,2-alkylene oxides which react with Precursor Z. Most preferably A is ethyleneoxy each occurrence and n is from about 4 to about 15.

PTP's can be used to increase the solubility of an alkali or alkaline earth metal salt in an organic medium. Preferred salts are sodium and potassium, while a preferred use of PTP's is in phase-transfer catalysts.

The PTP compounds are in many cases more effective phase-transfer catalysts than crown ethers or quaternary salts. The principle of phase-transfer catalysis involves two immiscible phases, with each phase containing a reactant. Adding a phase-transfer catalyst to this system, facilitates the reaction by causing one of the reactants to be soluble in the other phase. Both reactants are then in the same phase and the reaction can proceed at a more rapid rate. A detailed discussion of phase-transfer catalysis can be found in "Phase-Transfer Catalysis in Organic Synthesis" by W. P. Weber and G. W. Gokel (Springer-Verlag, 1977).

PTP's are exceptionally effective complexing agents for alkali or alkaline earth metal ions, such as sodium or potassium ions. In the present invention, this phase-transfer catalysis occurs when the inorganic salt is complexed by a PTP in an organic medium which comprises the organic reactant. PTP compounds of the present invention catalyze displacement reactions in two-phase systems without the use of special solvents such as dimethylformamide, dimethyl sulfoxide, hexamethylphosphoric amide, and the like. The displacement can be carried out in a non-polar solvent or if the organic reactant used in the displacement is liquid, then the reaction may take place in the absence of a solvent. The PTP's of the invention may also be used to catalyze dehydrohalogenation, condensation, carbene insertion, alkylation, oxidation, or reduction reactions, and other reactions which have been catalyzed by "crown ether" compounds. Examples of suitable reactions can be found in the Weber and Gokel reference and in "Principles and Synthetic Applications in Crown Ether Chemistry", *Synthesis*, 3, 168 (1976) by Gokel and Durst.

The following examples further illustrate the invention, but are not to be construed as limitations.

SPECIFIC EMBODIMENTS

EXAMPLE 1

Precursor Z is formed according to the procedure of A. M. Paquin in *Berichte*, 82, 316, 320 (1949) by acid catalysis of formaldehyde and monoethanolamine.

In a reaction vessel equipped with a pressure monitor gauge, a mixture of about one millimole of Z, about 18.2 millimoles of ethylene oxide and a catalytic amount of sodium hydroxide is slowly heated to about 105° C. with stirring. After 2–5 hours, the pressure in the vessel drops significantly. The vessel is then cooled and the residual pressure is carefully released. The thick oil formed is dissolved in methylene chloride, washed with a small amount of saturated ammonium chloride followed by a water-wash, then dried.

A mixture of about 820 mg of the oil, about 420 mg of n-butylbromide, about 5 ml of 50 percent aqueous sodium hydroxide and about 60 mg of tetra-n-butylammonium chloride is stirred at about 55° C. for about 15–16 hours. After cooling, methylene chloride is added to extract the organic layer. The extract is washed with saturated ammonium chloride, then dried and concentrated to about 950 mg of an oil. NMR shows the structure to be

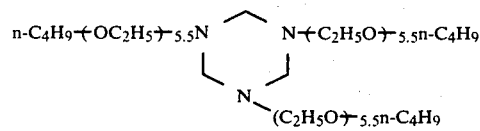

represented by the shorthand notation "PTP-EO$_{5.5}$-Bu", where "PTP" denotes the trifunctional perhydro-s-triazine moiety, "EO$_{5.5}$" indicates the average number of ethyleneoxy units in each "arm" of the product and "Bu" indicates that each "arm" is terminated with an n-butyl group (n-C$_4$H$_9$).

Other PTP compounds described below are prepared in a similar manner. Similar shorthand notation is used to designate the structure of these other PTP's.

EXAMPLES 2–9

The following reactions are carried out at about 80° C. using benzene as the solvent. The product formation is measured after 1 hour (in some instances, as noted, after 70 minutes) to determine the efficiency of the PTP as a catalyst. The results are shown in Table I, as Percent Reactant I converted to Product, determined by gas chromatography with 1,2,3,4-tetramethylbenzene internal standard.

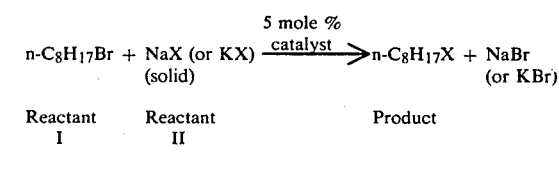

| | Reactant | | Reactant | | | Product | |
| | I | | II | | | | |

TABLE I

| | | Reactant II | | | | | |
|---|---|---|---|---|---|---|---|
| Example No. | Catalyst | NaOφ[a] | NaI | NaSCN | KI | KSCN | KY[b] |
| | | (Percent Reactant I Converted to Product) | | | | | |
| 2 | PTP—EO$_7$—Oc[d] | 52[c] | 55 | 30 | 77 | — | — |
| 3 | PTP—EO$_7$—H | 39[c] | — | — | — | — | — |
| 4 | PTP—EO$_{5.5}$—Oc | 39/51[c] | 100 | 58 | 74 | 57 | 28 |
| 5 | PTP—EO$_{5.5}$—Bu[e] | 43 | — | — | — | 46 | 59 |
| 6 | PTP—EO$_{5.5}$—H | 32 | — | — | — | 6 | — |
| 7 | PTP—EO$_4$—Oc | 25 | — | — | — | — | — |
| 8 | PTP—EO$_3$—Oc | 12 | — | — | — | — | — |

TABLE I-continued

| Example No. | Catalyst | Reactant II | | | | | |
|---|---|---|---|---|---|---|---|
| | | NaOφ[a] | NaI | NaSCN | KI | KSCN | KY[b] |
| | | (Percent Reactant I Converted to Product) | | | | | |
| 9 | PTP—EO$_2$—Oc | 10 | — | — | — | — | — |

Footnotes:
[a] Oφ = Phenate

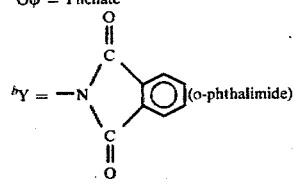

[b] Y = (o-phthalimide)

[c] after 70 minutes
[d] Oc = n-C$_8$H$_{17}$
[e] Bu = n-C$_4$H$_9$

I claim:
1. A compound of the formula

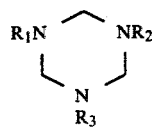

wherein $R_1$, $R_2$, and $R_3$ are independently $(-A-)_n R_4$, where —A— is independently, each occurrence —CHRCHR'O— wherein R and R' are hydrogen or methyl, provided that at most only one of R or R' is methyl, $R_4$ is independently, each occurrence, $C_{1-40}$ alkyl, and n is independently, each occurrence, a number from 2 to about 40.

2. The compound of claim 1 wherein $R_4$ is an alkyl group comprising from 3 to about 15 carbon atoms.

3. The compound of claim 1 wherein $R_4$ is octyl or butyl.

4. The compound of claim 1 or 3 wherein A is ethyleneoxy every occurrence and n is from about 4 to about 15.

5. The compound of claim 1 wherein, in every occurrence, $R_4$ is n-octyl, A is ethyleneoxy, and n is about 5.5.

* * * * *

UNITED STATES PATENT AND TRADEMARK OFFICE
CERTIFICATE OF CORRECTION

PATENT NO. : 4,266,054
DATED : May 5, 1981
INVENTOR(S) : Andrew T. Au

It is certified that error appears in the above—identified patent and that said Letters Patent is hereby corrected as shown below:

Under Abstract, line 7, "-perhydro-3-triazine" should read -- -perhydro-s-triazine--.

Column 2, line 54, "$B_4Br$" should read --$R_4Br$--.

Column 5, line 28, after the word 'are' insert --each--.

Signed and Sealed this

Twentieth Day of October 1981

[SEAL]

Attest:

GERALD J. MOSSINGHOFF

Attesting Officer    Commissioner of Patents and Trademarks